United States Patent [19]

Collins

[11] 4,297,902
[45] Nov. 3, 1981

[54] SAMPLER FOR MOLTEN MATERIAL AND A COMPONENT THEREOF

[76] Inventor: William J. Collins, 7005 Madison St., Fort Wayne, Ind. 46410

[21] Appl. No.: 75,941

[22] Filed: Sep. 17, 1979

[51] Int. Cl.³ .......................... G01N 1/12; G01N 1/20
[52] U.S. Cl. ............................... 73/863.33; 73/864.56
[58] Field of Search .................... 73/425.4 R, DIG. 9

[56] References Cited

U.S. PATENT DOCUMENTS

| | | | |
|---|---|---|---|
| 3,354,723 | 11/1967 | Smith | 73/425.6 |
| 3,656,346 | 4/1972 | Collins | 73/425.4 R |
| 3,859,857 | 1/1975 | Falk | 73/425.4 R |
| 3,897,689 | 8/1975 | Boron | 73/425.4 R |
| 4,002,072 | 1/1977 | Collins | 73/425.4 R |
| 4,002,074 | 1/1977 | Collins | 73/425.4 R |
| 4,007,640 | 2/1977 | Boron | 73/425.4 R |
| 4,046,016 | 9/1977 | Hackett | 73/425.4 R |
| 4,068,531 | 1/1978 | Collins | 73/425.4 R |

Primary Examiner—S. Clement Swisher
Attorney, Agent, or Firm—Charles S. Penfold

[57] ABSTRACT

The invention involves providing a device for sampling molten material which, among other things, comprises a pair of mating sections, each of which preferably has a rear recessed head and a front tubular formation, which when assembled provide a chamber and a pair of juxtaposed tubular formations which are adapted to respectively accommodate a pair of tubes, of which one or both may be utilized to receive such a material for flow into the chamber.

The invention also involves providing different forms of tubes and a method for making one of these tubes.

15 Claims, 20 Drawing Figures

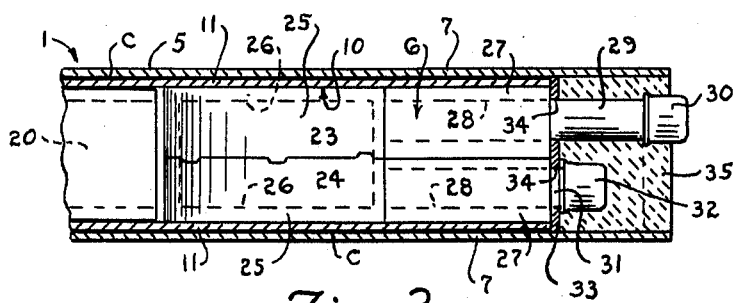
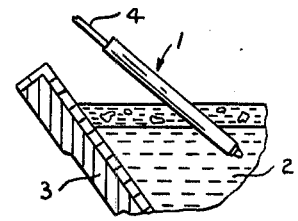
Fig.-2
Fig.-1
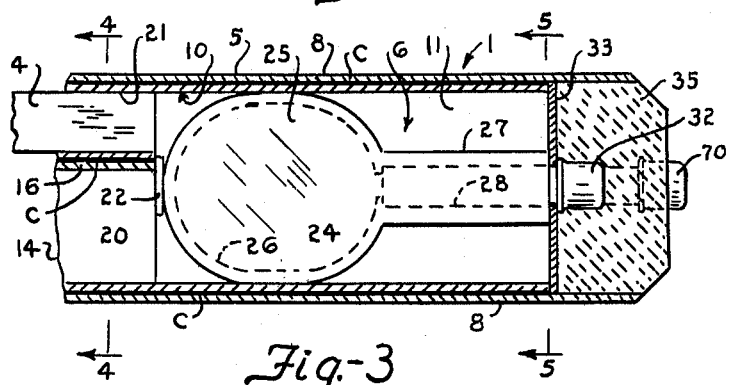
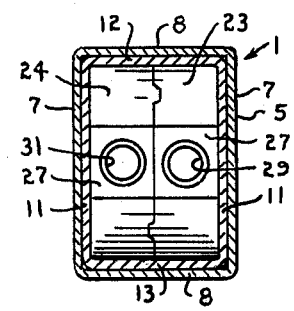
Fig.-3
Fig.-5
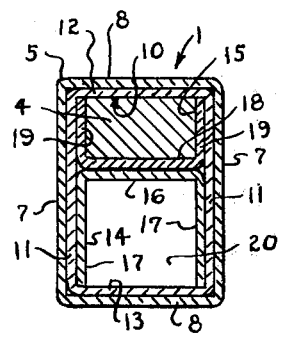
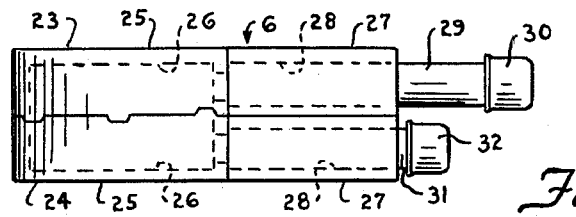
Fig.-4
Fig.-6
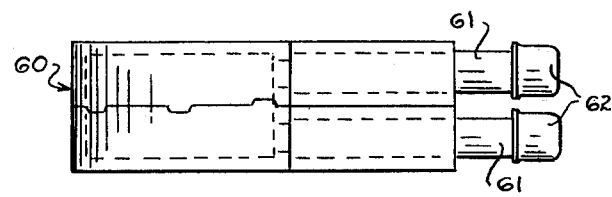
Fig.-8
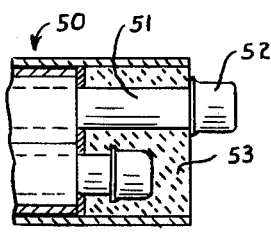
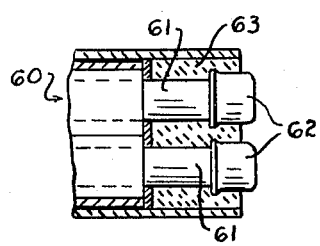
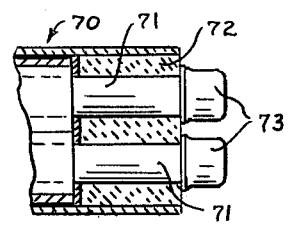
Fig.-7
Fig.-9
Fig.-10

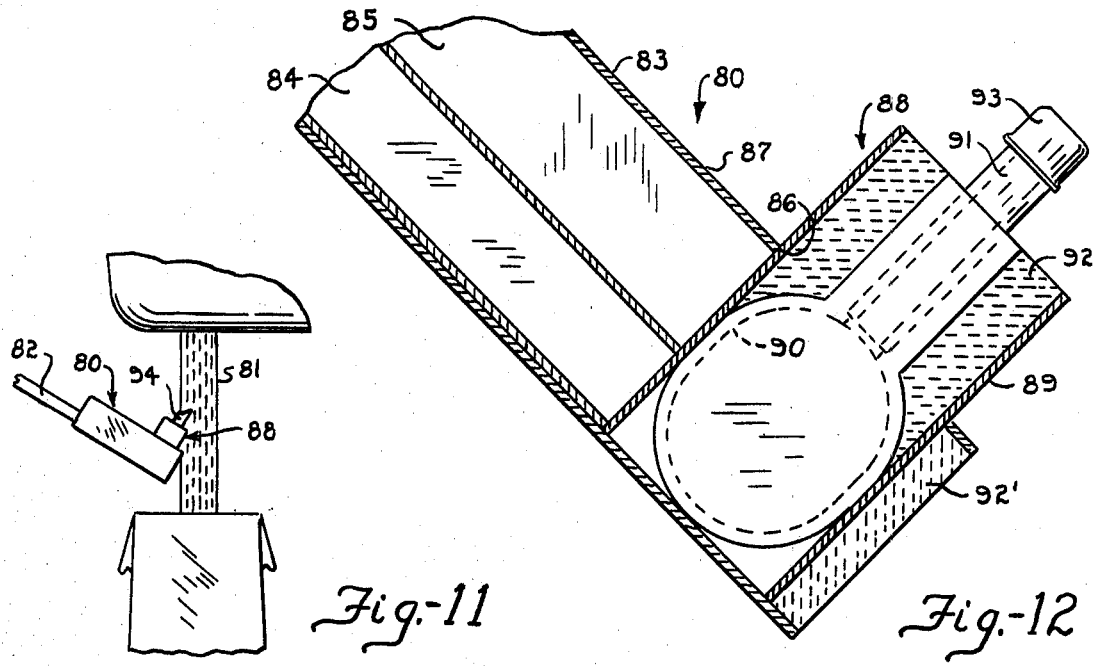
Fig.-11  Fig.-12
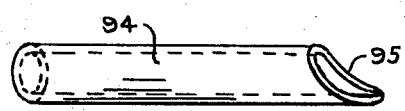 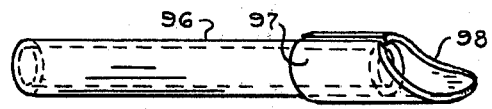
Fig.-13  Fig.-14
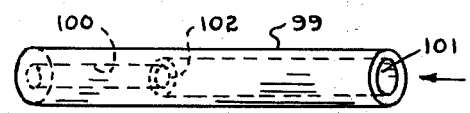
Fig.-15  Fig.-16
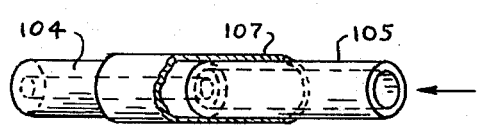
Fig.-17  Fig.-18
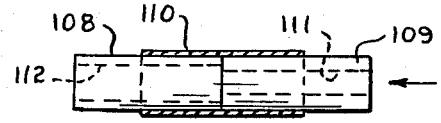 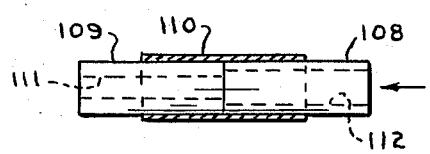
Fig.-19  Fig.-20

SAMPLER FOR MOLTEN MATERIAL AND A COMPONENT THEREOF

SUMMARY OF THE INVENTION

Appreciable development has been conducted by engineers with respect to providing various forms of devices for obtaining samples of molten material and many patents have issued directed to such devices. Quite a number of patents have issued to applicant in this regard and many are directed to devices, comprising, among other things, a pair of mating sections, each having a rear recessed head and a reduced front channel. These sections when assembled provide a chamber and a tubular formation in which a tubular inlet is secured for receiving molten material for flow into the chamber to obtain a sample.

OBJECTIVES

With the foregoing in mind, one of the principal objectives of the subject invention is to provide improvements over the structure described above and which preferably primarily involves providing each of the sections with a recessed head and a tubular formation, as distinguished from providing recessed heads and channels, the latter of which in combination provide a tubular formation.

A significant object of the invention is to provide an elongated structure having a rear extremity or means for detachable connection with a lance and a front tubular extremity having a partition therein for engagement by the tubular formations of the sections, and a mass of cement disposed in the front extremity against the partition and about the tubes for firmly securing the tubes in place.

A specific object is to provide abutment means in the structure in longitudinal spaced relation to the partition for holding the sections therebetween. The cross-sectional dimensions of the heads of the sections and cross-dimensions of the elongated structure are preferably such that the structure serves to hold the sections assembled and within the confines of the structure. In other words, the sections constituting a sub-assembly are press-fitted into the structure.

A particular object is to provide a device in which the tubes may be of corresponding or unequal lengths so that if so desired, the shorter tube can be embedded in cement, in which event, the molten material will first flow into the longer tube and then into the shorter one via the chamber, or if of corresponding lengths the material will flow through both tubes into the chamber.

Another object is to provide caps or closures for the tubes, the caps having inner portions which may or may not be embedded in the mass of cement in the front tubular extremity of the structure so that when at least one of the caps is melted, a forwardly extending portion of a tube initially closed thereby, some of the molten material will flow through the tube into the chamber formed by the heads of the mold sections.

A specific object of the invention is to provide various forms of tubes which may be utilized in conjunction with the mold sections.

Other objects reside in providing structure having components which can be manufactured and assembled on a production basis and one which is efficient in obtaining a sample.

Additional objects and advantages of the structure will become apparent after the description hereinafter set forth is considered in conjunction with the drawings annexed hereto.

Referring to the drawings:

FIG. 1 is a pictorial view showing the use of a sampler device in obtaining a sample of molten material from a vessel containing such a material;

FIG. 2 is a horizontal section taken through the front or fore extremity of structure for obtaining a sample of molten material;

FIG. 3 is a vertical section of the structure shown in FIG. 2;

FIG. 4 is a transverse vertical section taken substantially on line 4—4 of FIG. 3;

FIG. 5 is a vertical section taken on line 5—5 of FIG. 3;

FIG. 6 is a side elevational view of a subassembly for use with the structure of FIGS. 2 through 5;

FIG. 7 is a partial sectional view of a modified device related to FIG. 6;

FIG. 8 is a side elevational view of a modified assembly for use with the structure of FIG. 9; FIGS. 9 and 10 are partial sections of modified subassemblies for use with the structure of FIGS. 2 and 3;

FIG. 11 is a pictorial view showing a modified device of FIG. 12 being utilized to obtain a sample from a stream of molten material;

FIG. 13 is a pictorial view of a tubular means which is usable with the device of FIG. 12;

FIG. 14 is a pictorial view of a tubular means provided with a fitting whereby to facilitate entry of molten material into the tubular means;

FIG. 15 is a pictorial view of a modified tubular means having different internal cross-dimensions;

FIG. 16 is a horizontal section taken through FIG. 15 showing a material conditioning element disposed in the tubular means;

FIG. 17 is a pictorial view of a modified tubular means comprised of a pair of axially aligned members or tubes having different internal cross-dimensions and means for holding the members assembled;

FIG. 18 is a longitudinal section taken on FIG. 17 showing a material conditioning element positioned in the tubular means;

FIG. 19 is a horizontal view of a modified tubular means comprising a pair of members having different interanl cross-dimensions in which the one adapted for initially receiving a sample has a smaller internal cross-dimension; and FIG. 20 discloses that the structure of FIG. 19 may be reversed for use.

Referring first to FIG. 1 there is shown a sampler structure or device designated 1 immersed in a mass of molten material 2 in a vessel 3. A lance 4 is detachably connected to the device for manipulating the latter.

The structure disclosed in FIGS. 2 through 6 will now be described. This structure comprises an elongated outer housing designated 5 and an inner device or assembly generally designated 6 which serves to obtain a sample or samples from a supply of molten material.

More particularly, the housing 5 is preferably constructed from a suitable cellulosic material, such as pasteboard, and comprises a pair of parallel planar wide walls 7 and a pair of narrower parallel walls 8 to define a tubular multi-sided structure of rectangular cross-section. This housing has a rear extremity or means which serves to detachably accommodate an end of the lance 4 as shown in FIGS. 3 and 4, and a front extremity in which the device or subassembly 6 for obtaining a sample is secured. The device 6 is preferably secured in a tubular casing generally designated 10, also of pasteboard. This casing has side walls 11, and upper and lower walls 12 and 13.

The rear extremity may be designated and constructed in any manner desired but is preferably provided with a pair of internal channel members 14 and 15 as shown in FIG. 4. The member 14 is somewhat larger than the member 15 and has a top wall 16 and a pair of side walls 17 which engage the side walls 11 and lower wall 13 of the casing 10.

The channel member 15 has a bottom wall 18 engaging the top wall 16 of the member 14, and side walls 19 engaging the side walls 11 and upper wall 12 of the casing. The channel 14 below the upper channel forms in combination with the casing a tubular formation 20 which serves as a vent for the device and the upper channel 15 in combination with the casing serves to provide a tubular formation 21 for slidably detachably accommodating the lance 4. The channel members 14 and 15 are also preferably constructed of a cellulosic material and multi-sided and the cross-sectional dimensions of these components are such that the components can be readily slidably engaged to the positions desired and then preferably secured in place by adhesives C to provide a stable fabricated structure. Although the casing 10 is preferably secured in the outer housing and the channel members in the casing by cement it is to be understood that they can be secured in an assembled relation by staples of which one designated 22 of a pair is shown in FIG. 3 which serve as abutment means. If staples are not used, then the heads of the sections may be caused to engage one or both of the channels 14 and 15, so the latter will serve as abutment means.

The device 6 primarily comprises a pair of mating sections 23 and 24 and each includes a head 25 having a recess 26 and a reduced tubular formation 27 having a longitudinal opening 28 therein. When the sections are correctly assembled so that mating notches and projections on the sections are interengaged, the recesses 26 cooperate to provide a chamber for receiving a sample of the molten material. The opening in the section 23 serves to receive an inner extremity of a relatively long tubular means, tube or inlet 29 so that an outer extremity extends forwardly of the formation 27. A disintegratable or meltable closure or cap 30 is preferably press-fitted onto the tube for normally closing it. A tube 31 of a length less than the tube 29 is secured in the tubular formation of the section 24 and carries a closure or cap 32.

It should be noted that the front end of the casing 10 is inset a predetermined distance inwardly from the front marginal end edge of the outer housing 5. A partition 33 is disposed against the casing 10 and provided with a pair of holes 34 through which the tubular inlets 29 and 31 extend. The area in front of the partition 33 is preferably filled with a mass of insulation or cement 35 for surrounding or imbedding the shorter tube 31 and cap 32 thereon and surrounding the major portion of the larger tube 29 so that only a small portion extends beyond the free end of the mass for supporting the cap 30. This cement serves to protect the front extremity of the device and assists in holding the mating mold sections in the casing 10 and the partition 33 relative thereto. Only a minimum quantity of cement is required for the aforesaid purposes and it is preferably formed to extend forwardly to some extent as shown in FIGS. 2 and 3 to provide a protruding or nose-like formation. The sections 23 and 24 constitute a subassembly as depicted in FIG. 6, which can include the tubes and/or the casing 10.

A modified subassembly generally designated 50 is illustrated in FIG. 7 and substantially corresponds to the subassembly described above except that a tube 51 extends forwardly a greater distance than the tube 29 to receive a cap 52 which is not held by a mass of cement 53.

A modified subassembly generally designated 60 is illustrated in FIG. 8 for use in FIG. 9. This subassembly substantially corresponds to the subassembly of FIG. 6 or 7 and includes a pair of tubes 61 of substantially corresponding lengths which have caps or closures 62 secured thereto for at least partial embodiment in a mass of cement 63 as shown in FIG. 9.

A modified subassembly 70 is depicted in FIG. 10 and substantially corresponds to FIG. 9, except that a pair of tubes 71 are of a length greater than the tubes 61 and extend forwardly of a mass of cement 72 and support caps 73 which are detachable from the tubes 71.

When the structure of FIGS. 2 through 6 is utilized as intended, molten material will disintegrate or melt the cap 30 and flow into the chamber 26 through the tube 29 and then into the tube 31 to obtain sample portions conforming to the shape of the chamber 26 and tubes 29 and 31. If found desirable the cap 32 may be omitted, in which event, the mass of cement 35 will serve as a stop for molten material after flowing into the tube 31.

As to the structures depicted in FIGS. 9 and 10 it should be apparent that when at least portions of the caps melt or disintegrate, molten material will simultaneously flow into the chamber through a pair of tubes.

FIG. 11 depicts a modified structure or device generally designated 80 for use in obtaining a sample of molten material from a stream 81 thereof, structural details of the device being generally illustrated in FIG. 12. A lance 82 is detachably connectible to the device for manipulating it into and from the stream.

The structure of FIG. 12, preferably comprises an elongated tubular housing 83 provided with internal structure forming a pair of tubular formations 84 and 85 of which 84 is preferably utilized to accommodate the lance 82. A fore extremity of the housing is provided with an opening 86 in a side wall 87 thereof and a subassembly or device generally designated 88 is secured in the opening to locate it substantially transverse to the longitudinal axis of the housing.

The device 88 includes a casing 89 and a pair of mating sections are disposed in this casing and form a chamber 90 for receiving a sample of molten material which is adapted for inflow through a tubular means or tube 91. The sections are preferably held in the casing by a mass of cement or insulating material 92 which substantially surrounds reduced portions of the sections and additional cement 92' fills a void at the fore end of the housing 87 for the purposes of protection and stabilization. The tube 91 extends forwardly of the cement and a cap or closure 93 is preferably attached to the free end of the tube for the purpose of initially preventing the inflow of slag or foreign matter if the device is utilized for obtaining a sample from a mass in a vessel as depicted in FIG. 1 of it used according to FIG. 11 to obtain a sample from the stream 81 a tube such as 94 shown in FIG. 13 is preferably employed.

It is to be understood that the use of all of the structures or devices shown and described above can be utilized to obtain samples of molten material from any supply thereof, whether from a vessel or stream and that they are modifiable because their use depends on some measure on the character and liquidity of the material to be sampled. Otherwise expressed, the devices are designed and constructed for maximum versatility or convertability.

FIGS. 13 through 19 show different tubular means or tubes constructed of a non-metallic material, such as PYREX or quartz, for use in different sampling devices, including those described above.

FIG. 13 discloses the tube 94 usable with the structure of FIG. 11. It has a curved entrance 95 whereby to facilitate entry of molten material into the tube, as distinguished from a bevelled entrance.

FIG. 14 shows a tube 96 provided with a sleeve 97 which can be readily slipped onto the fore end of the tube whereby to facilitate entry of material through a curved or scalloped entrance 98. This sleeve is preferably of a split cylindical character so that it is resiliently flexible for clamping onto the tube. The sleeve also serves to protect the fore end of the tube. It should be noted that the sleeve is preferably located so that the fore end of the tube is positioned a predetermined distance inwardly from the fore end of the sleeve so as to promote the inflow of material into the tube.

FIGS. 15 and 16 disclose a tube 99 having a substantially uniform outside diameter, a pair of axially aligned cylindrical openings or passages 100 and 101 of different internal diameters or cross-dimensions. Due to the difference in these internal diameters a shoulder or abutment is formed to provide an annular seat 102 for a conditioning means, preferably in the form of a disc 103 of aluminum for deoxidizing the molten material as it flows into the passage 100 from the larger passage 99. The openings or passages 100 and 101 are preferably formed by boring them in the tube and this is considered to constitute a meritorious advance in the art.

FIGS. 17 and 18 show a pair of tubes 104 and 105 having corresponding outside diameters. The tube 105 which initially receives the molten material has a larger inside diameter or cross-dimension than the inside diameter of the opening or passage in tube 104. These tubes can be assembled as desired in an end-to-end relation, with a conditioning means 106 therebetween, such as that used in the tube of FIG. 16. The differences in the internal diameters allows placement of the conditioning means 106 so that a portion thereof is located in the tube 105 and against an inner end of the tube 104 and a portion is located in the latter. These tubes may be assembled together in end-to-end axial relationship by means preferably in the form of a piece of adhesive wrapping material 107.

The tube assembly shown in FIG. 19 preferably comprises a pair of tubes 108 and 109 which are preferably held together in an axial relationship by means, such as a piece of adhesive tape 110. The tube 109 has an internal passage 111 which has a cross-dimension or diameter less than that of a passage 112 in the tube 108. In some devices the assembly of FIG. 19 is utilized so that the molten material will first flow through the smaller passage and then into the larger passage 112 or if so desired the position of the assembly can be reversed as depicted in FIG. 20 so that the material will successively flow through passages 112 and 111, such utilization being dependent on the character of the molten material to be sampled, the source or supply from which the sample is obtained, and the liquidity of the material.

It is to be understood that if found desirable, the position of the structures of FIGS. 15 and 16 and 17 and 18 may also be reversed in a manner corresponding to FIGS. 19 and 20. It should also be obvious that in some instances the use of conditioning means such as identified as 103 and 106 respectively shown in FIGS. 16 and 18 may be eliminated.

It is to be further understood that the various tube structures or assemblies exemplified in FIGS. 15 through 20 are of such a character that they can be utilized in lieu of the tubes illustrated in FIGS. 2, 6, 8, 10, 11 and 12, depending at least on certain of the factors just alluded to and that the lengths of the tubes may be modified to suit different requirements.

Having thus described my invention or inventions, it is obvious that various modifications or additions to those described may be made in the same without departing from the spirit of the invention and, therefore, I do not wish to be understood as limiting myself to the exact forms, constructions, arrangements, and combinations of the components herein shown and described.

I claim:

1. A subassembly for use in obtaining a sample of molten material comprising a pair of mating sections, each of said sections having a recess and a tubular formation, said recesses when said sections are correctly assembled providing a chamber, and said tubular formations serving to respectively accommodate tubular means for the purposes described.

2. The subassembly defined in claim 1, including a pair of tubular means respectively secured in said tubular formations for receiving such material for flow into said chamber.

3. The subassembly defined in claim 1, including a pair of tubular means of different lengths respectively secured in said tubular formations.

4. A subassembly for use in obtaining a sample of molten material comprising a pair of mating sections, said sections having recesses forming a chamber and each section having a tubular formation, and a pair of tubular means respectivly secured in said tubular formations for receiving such a material for flow into said chamber.

5. The subassembly defined in claim 4, in which said tubular means are of different lengths.

6. A device for obtaining a sample of molten material comprising an outer elongated structure having a rear extremity for attachment to a lance and front tubular extremity, a pair of mating sections each of which has an enlarged recess and a tubular formation, said sections being positioned together in a casing in said front extremity whereby said recesses provide a chamber for receiving such a material, and a pair of tubular means having inner extremities respectively secured in said tubular formations and having outer ends for receiving such material for flow into said chamber.

7. The device defined in claim 6, including a partition disposed in said front extremity, said tubular formations engage said partition, said tubular means extend forwardly of said partition, and a mass of cement is disposed in said front extremity and substantially surrounds said means.

8. The device defined in claim 6, in which said elongated structure and said casing are of a multi-sided character.

9. A device for obtaining a sample of molten material comprising an outer elongated structure having a rear extremity for attachment to a lance and a front tubular extremity, a pair of mating sections each of which as an enlarged recess and a tubular formation, said sections being held together in said front extremity whereby said recesses provide a chamber for receiving such a material, a pair of tubular means through which such a material may be caused to flow having inner extremities respectively secured in said tubular formations and having outer ends, and meltable caps for normally closing said ends.

10. The device defined in claim 9, including a partition disposed in said front extremity, said tubular formations engage said partition, said tubular means extend forwardly of said partition, said tubular means extend forwardly of said partition, and a mass of cement is disposed in said front extremity and substantially surrounds said means.

11. A solid mold section having a recessed head and a reduced tubular formation, said section being cooperable with a mating section whereby the recess forms a chamber, and said tubular formation being constructed to receive tubular means through which a molten material may be caused to flow into the chamber.

12. In combination: an elongated tubular outer housing, an elongated tubular inner casing secured in said outer housing, a pair of mating sections forming a chamber and at least one of said sections having a tubular extension, a partition in said outer housing, tubular means extending through said partition and secured in said extension so a molten material may be caused to flow into said chamber, and a mass of cement is disposed in said housing against said partition and substantially surrounds said tubular means.

13. A subassembly for use in obtaining a sample of molten material comprising a pair of mating sections, said sections having recesses forming a chamber and each section having a tubular formation, a pair of tubular means respectively secured in said tubular formations, and means whereby one of said tubular means may be utilized to receive such a material for flow into the other tubular means via said chamber.

14. A subassembly for obtaining a sample of molten material, said subassembly forming a chamber, tubular means communicating with said chamber for receiving such a material for flow into said chamber, said tubular means comprising a pair of non-metallic tubes of which one has a greater internal cross-dimension than the internal cross-dimension of the other, and adhesive tape means securing said tubes together in axial alignment.

15. A subassembly for the purpose described comprising wall structure forming means for receiving some molten material from a supply thereof, and said wall structure also forming a pair of tubular formations serving to respectively accommodate tubular means for receiving such a material for flow into said receiving means.

* * * * *